United States Patent
Niessner et al.

(10) Patent No.: US 12,116,337 B2
(45) Date of Patent: *Oct. 15, 2024

(54) PROCESS FOR THE DEPOLYMERIZATION OF POLYSTYRENE

(71) Applicant: INEOS STYROLUTION GROUP GMBH, Frankfurt am Main (DE)

(72) Inventors: Norbert Niessner, Friedelsheim (DE); Bianca Wilhelmus, Hanau (DE); Achim Schmidt-Rodenkirchen, Bayreuth (DE); Konstantin Mierdel, Bayreuth (DE); Frank Neuner, Bayreuth (DE)

(73) Assignee: INEOS STYROLUTION GROUP GMBH, Frankfurt am Main (DE)

( * ) Notice: Subject to any disclaimer, the term of this patent is extended or adjusted under 35 U.S.C. 154(b) by 34 days.

This patent is subject to a terminal disclaimer.

(21) Appl. No.: 17/641,474

(22) PCT Filed: Sep. 17, 2020

(86) PCT No.: PCT/EP2020/075984
§ 371 (c)(1),
(2) Date: Mar. 9, 2022

(87) PCT Pub. No.: WO2021/053074
PCT Pub. Date: Mar. 25, 2021

(65) Prior Publication Data
US 2022/0324777 A1    Oct. 13, 2022

(30) Foreign Application Priority Data

Sep. 18, 2019  (EP) .................................. 19197959
Jan. 10, 2020  (EP) .................................. 20000009

(51) Int. Cl.
C07C 4/22    (2006.01)
C08J 11/12   (2006.01)

(52) U.S. Cl.
CPC ............... *C07C 4/22* (2013.01); *C08J 11/12* (2013.01); *C07C 2527/224* (2013.01); *C08J 2325/06* (2013.01)

(58) Field of Classification Search
CPC ..... C07C 4/22; C07C 2527/224; C07C 15/46; C08J 11/12; C08J 2325/06; Y02W 30/62
See application file for complete search history.

(56) References Cited

U.S. PATENT DOCUMENTS

| 5,672,794 A | 9/1997 | Northemann |
| 2012/0108863 A1* | 5/2012 | Tippet ...................... C07C 4/22 422/184.1 |

FOREIGN PATENT DOCUMENTS

| EP | 1481957 A1 | 12/2004 |
| EP | 1966291 A1 | 9/2008 |

(Continued)

OTHER PUBLICATIONS

Liu et al. "Pyrolysis of polystyrene waste in a fluidized-bed reactor to obtain styrene monomer and gasoline fraction", Fuel Processing Technology, vol. 63, No. 1, Mar. 1, 2000, pp. 45-55.

(Continued)

*Primary Examiner* — Thuan D Dang
(74) *Attorney, Agent, or Firm* — RAPHAEL BELLUM PLLC

(57) ABSTRACT

The invention relates to a process for the preparation of styrene monomers by depolymerising polystyrene, to a device for carrying out the process and to the use of a fluidised bed reactor for the depolymerisation of polystyrene. Said process comprising the following steps: a) feeding a polymer composition (A) containing 60 to 99.9 wt. polystyrene, based on the total weight of the polymer composition (A), into the reaction zone (R) of a pyrolysis reactor (P); b) thermally cracking the polystyrene contained in the polymer composition (A) in the reaction zone (R) of (Continued)

the pyrolysis reactor (P) at a temperature of between 400° C. to 1000° C. to obtain a product mixture (G) containing styrene monomers and other components; c) removing the product mixture (G) obtained in step b) from the reaction zone (R) of the pyrolysis reactor (P); d) cooling the product mixture (G) removed in step c) to obtain a condensed product mixture (K) containing styrene monomers and further components; and e) separating the styrene monomers from the further components of the condensed product mixture (K) obtained in step d), wherein the average residence time (Z) of the polymer composition (A) in the reaction zone (R) of the pyrolysis reactor (P) is from 0.01 sec to 10 sec.

18 Claims, 4 Drawing Sheets

(56) References Cited

FOREIGN PATENT DOCUMENTS

| | | |
|---|---|---|
| JP | H11-100875 A | 4/1999 |
| JP | 2005132802 A | 5/2005 |
| WO | 2018/018153 A1 | 2/2018 |

OTHER PUBLICATIONS

Samih Said et al.: "From complex feedstocks to new processes: The role of the newly developed microreactors" Chemical Engineering and Processing: Process Intensification 2018, 131, pp. 92-105).

Gabriela de la Puente et al., "Recycled Plastics in FCC Feedstocks: Specific Contributions", Industrial & Engineering Chemistry Research, vol. 36, No. 11, Nov. 1, 1997 (Nov. 1, 1997), pp. 4530-4534.

Konstantin I. Dement'ev et al., "Thermal depolymerization of polystyrene in highly aromatic hydrocarbon medium", Journal of Analytical and Applied Pyrolysis, May 5, 2019, vol. 142, pp. 1-10.

Williams et al., "Product composition from the fast pyrolysis of polystyrene", Environmental Technology, vol. 20, pp. 1109-1118 (1999).

Baskaran et al., "Anionic Vinyl Polymerization", Controlled and Living Polymerizations: From Mechanisms to Applications, John Wiley & Sons, 2009, pp. 1-56.

Achilias et al., "Chemical recycling of polystyrene by pyrolysis: Potential Use of the Liquid Product for the Reproduction of Polymer", Macromolecular Materials and Engineering, 292(8) (2007), pp. 923-934.

C. Bouster, "Evolution of the Product Yield With Temperature and Molecular Weight in the Pyrolysis of Polystyrene", Journal of Analytical and Applied Pyrolysis 15 (1989) 249-259.

C. Bouster et al., "Study of the Pyrolysis of Polystyrenes: Kinetics of Thermal Decomposition", Journal of Analytical and Applied Pyrolysis, 1 (1980) 297-313.

Grause et al., "Feedstock recycling of polymeric waste material", Journal of Material Cycles and Waste Management, 13(4), 2011, 265-282.

A. Echte et al., "Half a Century of Polystyrene—A Survey of the Chemistry and Physics of a Pioneering Material", Angew. Chem. (Int. Ed. Engl.) 20, 344-361 (1981).

* cited by examiner

PROCESS FOR THE DEPOLYMERIZATION OF POLYSTYRENE

The invention relates to a process for the production of styrene monomers by depolymerization of polystyrene, to an apparatus for conducting the process and to the use of an apparatus for the depolymerization (breakdown) of polystyrene.

Polystyrene is preferably selected from the group consisting of: standard polystyrene (GPPS), high impact polystyrene (HIPS), styrene-butadiene copolymers. Particular preference is given to high impact polystyrene (HIPS) and/or standard polystyrene. High impact polystyrenes (HIPSs) and standard polystyrenes, and also their production, structure and properties, are described extensively in review literature (A. Echte, F. Haaf, J. Hambrecht in Angew. Chem. (Int. Ed. Engl.) 20, 344-361 (1981); and also in the Kunststoffhandbuch [Plastics Handbook], edited by R. Vieweg and G. Daumiller, Volume 4 "Polystyrol" [Polystyrene], Carl Hanser Verlag, Munich (1996).

The transition from a linear to a circular economy is necessary both ecologically and economically from the viewpoints of climate change, environmental pollution, population growth and dependence on resources. As early as in the 1980s and 1990s, intense efforts were directed towards the development of processes for the feedstock recycling of plastics wastes, but no industrial applications have arisen to date due to unresolved process-technological problems and for economic reasons. Due to generally increasing environmental awareness and the rising need for sustainable solutions, however, interest in chemical recycling is growing as well.

Not all thermoplastic polymers are equally well suited to chemical recycling. The thermal decomposition of polyolefins or polyesters forms mixtures of, inter alia, waxes, light oil and gases. The breakdown of polyethylene terephthalate (PET) results in organic acids, predominantly benzoic acid and terephthalic acid, which are corrosive and may also cause blockage of the reactor (G. Grause et al., Rohstoffrecycling von polymerem Abfallmaterial [Feedstock recycling of polymeric waste material], in: Journal of Material Cycles and Waste Management, 13(4), 2011, 265-282).

In the case of polystyrene and other styrene-containing polymers, it is possible to depolymerize these polymers into their base constituents, especially styrene monomers, and for this reason polystyrene and other styrene monomer-containing polymers represent an exceptional choice for chemical recycling.

However, the product mixture resulting from a depolymerization process must be purified in order to use the components as a feedstock for new purposes, such as polymerization processes.

When polystyrene is thermally treated to a sufficient extent, it decomposes into styrene monomers, but incomplete decomposition also leads to the formation of, for example, styrene dimers and trimers and other oligomers. If the decomposition conditions are too harsh, byproducts such as benzene, toluene, ethylbenzene, cumene and alpha-methylstyrene may be formed. The amounts of these reaction products vary and depend on the reaction conditions and the feedstocks used (see C. Bouster et al., Study of the pyrolysis of polystyrenes: Kinetics of thermal decomposition, Journal of Analytical and Applied Pyrolysis, 1 (1980) 297-313 and C. Bouster, Evolution of the product yield with temperature and molecular weight in the pyrolysis of polystyrene, in: Journal of Analytical and Applied Pyrolysis 15 (1989) 249-259).

The styrene monomers obtained can be used for a new polymerization process. Styrene oligomers may possibly disrupt the polymerization process, since they influence important properties of the polymer even in small amounts. This also applies to other byproducts. Therefore, the styrene monomers should be separated from other components of the product mixture in order to ensure a high product quality.

In particular, aromatic compounds other than styrene monomers can act in free-radical polymerization processes as chain-transfer agents, which lower the average molecular weight of the polymers produced and contribute to polymers having a lower glass transition temperature (Tg) (see DS Achilias et al., Chemical recycling of polystyrene by pyrolysis: Potential use of the liquid product for the reproduction of polymer, in: Macromolecular Materials and Engineering, 292(8) (2007), 923-934). Protons from, for example, carboxylic acids, alcohols, aldehydes or ketones, act as terminators in anionic styrene polymerization processes (see D. Baskaran, Anionic Vinyl Polymerization, in: Controlled and Living Polymerizations: From Mechanisms to Applications, John Wiley & Sons, 2009, 1-56).

In the present process, polystyrene preferably selected from the group of standard polystyrene (GPPS), high impact polystyrene (HIPS) and styrene-butadiene copolymers is used. Furthermore, the high impact polystyrenes used may have been structurally modified compared to conventional rubbers through the use of specific polybutadiene rubbers with for example a modified 1,4-cis and/or 1,4-trans fraction or 1,2- and 1,4-bond.

In addition, instead of polybutadiene rubber it is also possible to use other diene rubbers and elastomers of ethylene-propylene-diene copolymer type (EPDM rubber) and also hydrogenated diene rubbers or else silicone rubbers.

In the impact-resistant polystyrene used as polystyrene, the diene rubber content, in particular the polybutadiene rubber content, is generally 5% to 12% by weight, preferably 6% to 10% by weight, particularly preferably 7% to 9% by weight, and the polystyrene content is generally 88% to 95% by weight, preferably 90% to 94% by weight, more preferably 91% to 93% by weight, the sum of polystyrene content and diene rubber content giving 100% by weight.

Suitable standard polystyrene is produced by the method of anionic or free-radical polymerization. In this case, the molecular weight inhomogeneity of the polymer which can be influenced by the polymerization process is of minor importance. Preference is given to standard polystyrene and high impact polystyrene the toluene-soluble fraction of which has an average molecular weight Mw of 150 000 to 300 000 g/mol, particularly preferably 150 000 to 270 000 g/mol, and which is optionally further provided with additives, such as for example mineral oil (e.g. white oil), stabilizers, antistats, flame retardants or waxes.

Styrene copolymers used as polystyrene may contain methyl (meth)acrylate, α-methylstyrene and/or maleic anhydride, and other copolymerizable monomers.

JP 2005132802 and JPH 11100875 (Toshiba Plant Systems) describe a process for the recovery of styrene from polystyrene wastes, however, no solution is provided for the separation of low boilers, styrene and high boilers.

There is a great need for a process for the production of styrene monomers by depolymerization of polystyrene, which affords styrene in a very high yield and in which the formation of styrene oligomers is kept to a minimum, in order to minimize the subsequent purification process.

It is known that the fluidized bed process is suitable for the depolymerization of polymers, such as, inter alia, polystyrene. Liu et al. ("Pyrolysis of polystyrene waste in a fluidized-bed reactor to obtain styrene monomer and gasoline fraction", Fuel Processing Technology, 63, 45-55 (2000)) and Williams et al. ("Product composition from the fast pyrolysis of polystyrene", Environmental Technology, 20, 1109-1118 (1999)) investigate the pyrolysis of PS wastes by means of a fluidized bed reactor and in the process observe the depolymerization of polystyrene into styrene monomers and oligomers.

An object of the invention is that of providing a process for the production of styrene monomers by depolymerization of polystyrene with optimized process conditions in order to maximize the yield of styrene monomers. Harmful byproducts should also be avoided.

It has been found that certain combinations of depolymerization temperature and residence time in the reactor result in particularly high styrene monomer yields.

The invention provides a process for the production of styrene monomers by depolymerization of polystyrene, comprising the steps of:
  a) feeding a polymer composition (A) containing 60% to 99.9% by weight of polystyrene, based on the total weight of the polymer composition (A), into the reaction zone (R) of a pyrolysis reactor (P);
  b) thermally cleaving the polystyrene present in the polymer composition (A) in the reaction zone (R) of the pyrolysis reactor (P) at a temperature of from 450° C. to 1000° C., in order to obtain a product mixture (G) containing styrene monomers and further components;
  c) withdrawing the product mixture (G) obtained in step b) from the reaction zone (R) of the pyrolysis reactor (P);
  d) cooling the product mixture (G) withdrawn in step c), in order to obtain a condensed product mixture (K) containing styrene monomers and further components; and
  e) separating the styrene monomers from the further components of the condensed product mixture (K) obtained in step d),
  wherein the average residence time (Z) of the polymer composition (A) in the reaction zone (R) of the pyrolysis reactor (P) is from 0.01 s to 10 s.

The polymer composition (A) which in the process according to the invention in step a) is fed into the reaction zone (R) of the pyrolysis reactor (P), contains 60% to 99.9% by weight, preferably 80% to 99.9% by weight, particularly preferably 90% to 99.9% by weight, very particularly preferably 95% to 99.9% by weight, of polystyrene, based on the total weight of the polymer composition (A).

The remaining 0.1% to 40% by weight, preferably 0.1% to 20% by weight, particularly preferably 0.1% to 10% by weight, very particularly preferably 0.1% to 5% by weight, based on the total weight of the polymer composition (A), may be polymeric components other than polystyrene and/or additives and/or other foreign substances.

If the polymer composition (A) contains polymers other than polystyrene, these are selected, by way of example, from the group consisting of polyolefins, polyesters, (co)polymers of acrylonitrile, (co)polymers of vinylaromatic monomers other than styrene, (co)polymers of alkyl (meth)acrylates and copolymers of styrene with other monomers which do not belong to the other (co)polymers listed here.

Suitable as polymers other than polystyrene are, by way of example, copolymers of vinylaromatic monomers with further comonomers such as butadiene, (meth)acrylate, acrylonitrile, alpha-methylstyrene and phenylmaleimide. In particular these are vinylaromatic copolymers selected form the group consisting of: styrene-acrylonitrile copolymers (SAN), α-methylstyrene-acrylonitrile copolymers (AMSAN), styrene-maleic anhydride copolymers, styrene-phenylmaleimide copolymers, styrene-methyl methacrylate copolymers (SMMA), styrene-acrylonitrile-maleic anhydride copolymers, styreneacrylonitrile-phenylmaleimide copolymers, α-methylstyrene-acrylonitrile-methyl methacrylate copolymers, α-methylstyrene-acrylonitrile-t-butyl methacrylate copolymers and styrene-acrylonitrile-t-butyl methacrylate copolymers.

Also suitable as other polymers are, for example, diene rubbers such as homopolymers of conjugated dienes and copolymers of such dienes with one another, copolymers of such dienes with acrylates, in particular n-butyl acrylate, and copolymers of such dienes with the comonomers selected from styrene, α-methylstyrene, acrylonitrile, methacrylonitrile, methyl methacrylate (MMA), maleic anhydride (MA) and Nphenylmaleimide (N-PMI). The diene rubbers can also contain crosslinking, polyfunctional monomers.

Also suitable are polyolefins such as PE-LD (low-density polyethylene), PE-LLD (linear low-density polyethylene), PE-HD (high-density polyethylene), metallocene polyethylenes, ethylene copolymers such as poly(ethylene-co-vinyl acetate), ethylene-butene, ethylene-hexene, ethylene-octene copolymers, and also cycloolefin copolymers, individually or as a mixture. Also useful are, for example, polypropylenes such as homo- or copolymers of propylene, metallocene-catalyzed polypropylenes and copolymers of propylene with other comonomers known to those skilled in the art.

The polymer composition (A) may likewise contain polycarbonates, polyamides, poly(meth)acrylates, polyvinylchlorides, polyesters, halogenated polymers, vinylaromatic diene copolymers (SBC), polyethers, polysulfones, polyethersulfones, polyimidazoles and related polymers.

The polymer composition (A) preferably contains less than 30% by weight, particularly preferably less than 15% by weight, very particularly preferably less than 5% by weight of polyolefins, based on the total weight of the polymer composition (A), less than 5% by weight, particularly preferably less than 2% by weight, very particularly preferably less than 1% by weight of (co)polymers of acrylonitrile, based on the total weight of the polymer composition (A), and less than 5% by weight, particularly preferably less than 2% by weight, very particularly preferably less than 1% by weight of polyesters, based on the total weight of the polymer composition (A).

The polymer composition (A) preferably does not contain any polymeric components other than polystyrene.

Additives present in the polymer composition (A) can be 0% to 20% by weight of customary plastics additives and auxiliaries, based on the total weight of the polymer composition (A). By way of example, an additive or an auxiliary can be selected from the group consisting of antioxidants, UV stabilizers, peroxide destroyers, antistats, lubricants, mold-release agents, flame retardants, fillers or reinforcers (glass fibers, carbon fibers, etc.), colorants and combinations of two or more of these. As examples of oxidation retarders and heat stabilizers, mention is made of halides of metals of group I of the periodic table, e.g. sodium halides, potassium halides and/or lithium halides, possibly in conjunction with copper(I) halides, e.g. chlorides, bromides, iodides, sterically hindered phenols, hydroquinones, various substituted representatives of these groups and mixtures thereof in concentrations of up to 1% by weight, based on the total weight of the polymer composition (A).

As UV stabilizers, which are generally present in amounts of up to 2% by weight, based on the total weight of the polymer composition (A), mention may be made of various substituted resorcinols, salicylates, benzotriazoles and benzophenones.

Organic dyes such as nigrosin, pigments such as titanium dioxide, phthalocyanines, ultramarine blue and carbon black, may also be present as colorants in the polymer composition (A), and also fibrous and pulverulent fillers and reinforcing agents. Examples of the latter are carbon fibers, glass fibers, amorphous silica, calcium silicate (wollastonite), aluminum silicate, magnesium carbonate, kaolin, chalk, powdered quartz, mica and feldspar.

Examples of nucleating agents present may be talc, calcium fluoride, sodium phenylphosphinate, aluminum oxide, silicon dioxide and nylon 22.

Examples of lubricants and mold-release agents, which may generally be used in amounts of up to 1% by weight, based on the total weight of the polymer composition (A), are long-chain fatty acids such as stearic acid or behenic acid, their salts (e.g. Ca stearate or Zn stearate) or esters (e.g. stearyl stearate or pentaerythritol tetrastearate) and also amide derivatives (e.g. ethylenebisstearylamide).

Mineral-based antiblocking agents may moreover be present in amounts of up to 0.1% by weight, based on the total weight of the polymer composition (A). Examples that may be mentioned include amorphous or crystalline silica, calcium carbonate and aluminum silicate.

As processing aid, mineral oil, preferably medicinal white oil, may for example be present in amounts of up to 5% by weight, preferably up to 2% by weight, based on the total weight of the polymer composition (A).

As examples of plasticizers, mention may be made of dioctyl phthalate, dibenzyl phthalate, butyl benzyl phthalate, hydrocarbon oils, N-(n-butyl)benzenesulfonamide and o- and p-tolylethylsulfonamide.

Any of the flame retardants known for the respective thermoplastics may moreover be present, in particular those based on phosphorus compounds or red phosphorus.

Furthermore, moisture and/or further inorganic and/or organic foreign constituents, such as for example foodstuff residues, may also be present.

In a particularly preferred embodiment, the polymer composition (A) consists of 90% to 99.9% by weight of polystyrene, based on the total weight of the polymer composition (A), and 0.1% to 10% by weight of additive(s), based on the total weight of the polymer composition (A). In a very particularly preferred embodiment, the polymer composition (A) consists of 95% to 99.9% by weight of polystyrene, based on the total weight of the polymer composition (A), and 0.1% to 5% by weight of additive(s), based on the total weight of the polymer composition (A).

Preferably, the polystyrene component which is present in the polymer composition (A) consists essentially, preferably completely, of GPPS (general purpose polystyrene). In this context, "essentially" means that no constituents which modify the properties of the GPPS in a significant way are present in the polystyrene component.

The polymer composition (A) used according to the invention may optionally be pretreated in a suitable manner, for example in order to remove adherent contaminants such as for example foodstuff residues or dirt, moisture and foreign substances such as metals or other substances and composite materials.

This is advantageously effected in a pretreatment, which may comprise one or more of the following steps, where the sequence of the steps is not fixed and steps may also be repeated multiple times: manual impurity sorting, washing, comminution, automatic sorting in suitable plants. Optionally, polymer compositions which do not correspond to the polymer composition (A) may also be converted by such a process into a polymer composition (A) used according to the invention.

Preference is therefore also given to an embodiment of the process according to the invention in which a polymer composition which does not correspond to the polymer composition (A) is subjected to a pretreatment, comprising one or more of the following steps, where the sequence of the steps is not fixed and steps may also be repeated multiple times: manual impurity sorting, washing, comminution, automatic sorting in suitable plants, in order to thus obtain the polymer composition (A).

The thermal decomposition of the polystyrene can take place in any suitable reactor in which the temperature required for the decomposition can be achieved. For example, the thermal decomposition can be performed in a rotary kiln. Rotary kilns are described for example in EP-A 1481957. The thermal decomposition may also take place in extruders, these are described for example in EP-A 1966291. Such reactors can be operated with or without a gas stream, such as carrier gas or gas as reaction medium.

The pyrolysis reactor (P) can accordingly in principle be any known type of pyrolysis reactor, with the proviso that the design of the pyrolysis reactor allows a precise setting of the temperature in the reaction zone (R) of the pyrolysis reactor (P) and a precise setting of the average residence time (Z) of the polymer composition (A) in the reaction zone (R) of the pyrolysis reactor (P).

In this context, "precise setting" means that the deviation of the actual temperature in the reaction zone (R) of the pyrolysis reactor (P) from the set temperature is at most 10° C., preferably at most 5° C., particularly preferably at most 1° C., and that the deviation of the actual average residence time (Z) from the set average residence time (Z) is at most 0.2 s, preferably at most 0.1 s, particularly preferably at most 0.05 s, very particularly preferably at most 0.01 s.

The pyrolysis reactor (P) is preferably a fluidized bed reactor, described for example in Schildhauer et al., "Reaktoren für Fluid-Feststoff-Reaktionen: Wirbelschichtreaktoren" [Reactors for fluid-solid reactions: fluidized bed reactors], in: Reschetilowski W. (ed.): Handbuch Chemische Reaktoren [Handbook of chemical reactors], Springer Spektrum, Berlin, Heidelberg (2019). Typically, a gas or gas mixture is used as a fluidization medium here. The gas or gas mixture is typically unreactive under the conditions prevailing in the pyrolysis reactor (P). Preferably, the gas is selected from steam, nitrogen, noble gases (Xe, Ar, Ne, He) or a mixture thereof.

The gas or gas mixture can be introduced into the pyrolysis reactor (P) as a separate gas stream. The optimal flow rate of the gas or gas mixture depends on the reactor configuration and on the reaction or process conditions.

Optimization of the process is possible via the parameters of temperature, residence time of the reaction mixture in the reaction zone (R) of the pyrolysis reactor (P) and concentration of the starting materials. The region of the reactor in which the reaction mixture is subjected to those conditions at which depolymerization reactions take place is referred to here as the reaction zone (R).

The pyrolysis reactor (P) can contain a solid medium, e.g. $SiO_2$ (quartz sand) or SiC. In a preferred embodiment, the pyrolysis reactor (P) is a fluidized bed reactor which comprises a fluidized bed of silicon carbide (SiC) in the reaction zone (R). In addition to a high chemical and mechanical stability, SiC possesses good thermal conduction and heat capacity. This combination is advantageous for conducting endothermic processes.

Preference is given to using SiC having a weight-average particle size of from 20 to 1000 μm, particularly preferably from 40 to 500 μm. Such particle sizes achieve a particularly good fluidization of the fluidized bed and enable particularly effective heat transfer to the polymer composition (A).

It has been found that the yield of styrene monomers is particularly high when the residence time of the polystyrene in the depolymerization zone is chosen to be short. This can be achieved in fluidized bed reactors or other reactors which use a gas stream for the transport of the introduced polymer composition (A) through the reactor. The average residence times of the reaction material are between 0.1 second and 10 seconds. Short residence times can be achieved using high flow rates for the gas stream. The depolymerization can be conducted at pressures of from 0.01 bar to 5 bar, or at atmospheric pressure (1 bar). The gas stream is preferably preheated before it is conveyed into the reaction zone (R). The preheating is preferably effected at a temperature which is not more than 200° C. below the temperature in the reaction zone (R) of the pyrolysis reactor (P).

The temperature in the reaction zone (R) of the pyrolysis reactor (P) in the process according to the invention is set to 400 to 1000° C., often 450 to 1000° C., preferably to 500 to 800° C., particularly preferably to 550 to 650° C., very particularly preferably to 580 to 630° C., and the average residence time of the polymer composition (A) in the reaction zone (R) of the pyrolysis reactor (P) is set to 0.1 to 10 s, preferably to 0.2 to 2 s, particularly preferably to 0.3 to 1 s, very particularly preferably to 0.4 to 0.6 s. In a preferred embodiment, the temperature in the reaction zone (R) is 500 to 800° C., and the average residence time of the polymer composition (A) therein is 0.2 to 2 s. In a particularly preferred embodiment, the temperature in the reaction zone (R) is 550 to 650° C., and the average residence time of the polymer composition (A) therein is 0.3 to 1 s. In a very particularly preferred embodiment, the temperature in the reaction zone (R) is 580 to 630° C., and the average residence time of the polymer composition (A) therein is 0.4 to 0.6 s.

The temperature can be set in any known way, for example by microwave radiation, using heat exchangers, gas burners, resistive heating conductors (resistance heating), or by introducing superheated gas, in particular steam, on their own or in combination. In one embodiment, the temperature is set using resistive heating conductors which are in contact with the wall of the reaction zone (R) of the pyrolysis reactor (P). Alternatively, the temperature can be set using steam, which is provided by evaporating water and is brought to the desired temperature by means of a steam superheater. In one embodiment, a combination of resistive heating conductors in contact with the wall of the reaction zone (R) of the pyrolysis reactor (P) and steam is used to set the temperature in the reaction zone (R) of the pyrolysis reactor (P).

In a preferred embodiment, the pyrolysis reactor (P) is a fluidized bed reactor, preferably comprising an SiC fluidized bed in the reaction zone (R) thereof, the temperature in the reaction zone (R) being set by introducing steam having the desired temperature. In this embodiment, the steam is provided by an evaporator and is brought to the desired temperature by means of a steam superheater. In this embodiment, the steam is also used both to set the temperature in the reaction zone (R) and to create the fluidized bed. Optionally, in this embodiment, the heat energy in the reaction zone (R) can be additionally provided by resistive heating conductors which are in contact with the wall of the reaction zone (R) of the pyrolysis reactor (P).

The particle size and the concentration of the polymer composition (A) in the reaction zone (R) can be adapted to the specific conditions of the reactor and its configuration, to the reaction conditions and to the composition of the polymer composition (A). The polymer composition (A) typically has a particle size of between 100 μm and 50 mm, preferably between 250 μm and 5 mm, particularly preferably between 500 μm and 2 mm. The particles may be of spherical or nonspherical form. In the case of a spherical form, the particle size is determined by measuring the volume-average diameter. In the case of nonspherical particles, for example needle-shaped particles, the longest dimension is used for determination of the particle size.

The concentration of the reaction material in the reactor depends on the reactor type, the reactor size and the reactor configuration. The concentration of the polymer composition (A) in the reaction zone (R) of the pyrolysis reactor (P) is typically between 1% and 50% by weight, preferably between 1% and 25% by weight, particularly preferably between 1% and 10% by weight, very particularly preferably between 2% and 7% by weight.

Preferably, the polymer composition (A) in step a) is pneumatically fed into the reaction zone (R) of the pyrolysis reactor (P), mixed with the fluidized bed of silicon carbide and lastly depolymerized in step b). Particular preference is given to continuously feeding in the polymer composition (A) in step a).

During the residence time (Z) in the reaction zone (R) of the pyrolysis reactor (P), the polystyrene component and possibly other polymers in the polymer composition (A) are at least partly depolymerized in order to give a product mixture (G) containing styrene monomers and other components.

The product mixture (G) containing styrene monomers and other components is withdrawn from the reaction zone (R) of the pyrolysis reactor (P) in step c). Withdrawal preferably takes place continuously. Particularly preferably, the product mixture (G) is continuously withdrawn in the gas state from the upper region of the reaction zone (R) of the pyrolysis reactor (P). In this case, the product mixture (G) may for example be withdrawn automatically by transport of the product mixture (G) out of the reaction zone (R) due to the elevated pressure in the reaction zone (R) brought about by the reaction.

The pyrolysis reactor may contain a quencher or be connected to a quencher. In this context, a quencher is understood to be a region of the pyrolysis reactor in which the depolymerization reaction is rapidly halted, preferably by cooling the hot gas consisting of the product mixture (G) and inert gas stream, preferably steam. The quencher serves, inter alia, for stabilization of the reaction products and for preventing or reducing undesired repolymerization. Typical quenchers cool the product mixture (G) from a temperature of more than 400° C. to a temperature of less than 350° C. within a very short time, preferably within fewer than 10 seconds, particularly preferably within fewer than 5 seconds, particularly preferably within less than 1 second. Quenchers are described for example in EP 1966291.

The product mixture (G) is cooled down after withdrawal from the reaction zone (R) of the pyrolysis reactor (P), resulting in the condensation of the styrene monomers and further components and the obtaining of a condensed product mixture (K) containing styrene monomers and further components. The product mixture (G) is cooled down to a temperature below the condensation point of styrene monomers. The product mixture (G) is preferably cooled to a temperature below 70° C., particularly preferably below 50° C., very particularly preferably below 40° C. In a preferred embodiment, the product mixture (G) is cooled to a temperature of from 0° C. to 70° C. In a particularly preferred embodiment, the product mixture (G) is cooled to a temperature of from 0° C. to 50° C. In a very particularly preferred embodiment, the product mixture (G) is cooled to a temperature of from 15° C. to 40° C.

The cooling can be effected in any known manner. For example, cooling on a solid surface which is cooled by water or air is possible. Likewise possible is cooling by means of a water mist which is brought directly into contact with the product mixture (G). The cooling preferably takes place in a water mist.

Here, the condensable constituents of the product mixture (G) are condensed according to their vapor pressures and collected together with the water. A condensed product mixture (K) containing styrene monomers and further constituents is obtained in the condensation. In the case of cooling in a water mist, the condensed product mixture (K) is obtained as a two-phase system with the cooling water. In this case, the condensed product mixture (K) is separated from the aqueous phase as a floating organic phase. The aqueous phase can be cooled again and used as water mist for cooling the product mixture (G).

The condensed product mixture (K) typically contains more than 50% by weight of styrene monomers, based on the total weight of the condensed product mixture (K), and less than 50% by weight of the further constituents, based on the total weight of the condensed product mixture (K). Preferably, the condensed product mixture (K) contains 50% to 99% by weight of styrene monomers, based on the total weight of the condensed product mixture (K), and 1% to 50% by weight of the further constituents, based on the total weight of the condensed product mixture (K), particularly preferably 60% to 99% by weight of styrene monomers, based on the total weight of the condensed product mixture (K), and 1% to 40% by weight of the further constituents, based on the total weight of the condensed product mixture (K), very particularly preferably 75% to 99% by weight of styrene monomers, based on the total weight of the condensed product mixture (K), and 1% to 25% by weight of the further constituents, based on the total weight of the condensed product mixture (K).

In the further course of the process, the condensed product mixture (K) is separated into styrene monomers and further constituents. This separation can be conducted in any known manner which is suitable for separating mixtures of liquid products and possibly solids into their constituents. Depending on the further constituents besides styrene monomers, suitable methods for separating the condensed product mixture (K) into styrene monomers and further constituents may for example comprise sedimentation, centrifugation, filtration, decantation, distillation, chromatography, crystallization and sublimation.

If solids are present in the condensed product mixture (K), it is advantageous to remove the solids prior to separation of the liquid constituents. In this case it is preferable to remove the solids from the liquid constituents by sedimentation, centrifugation, filtration, distillation, sublimation and/or decantation, particularly preferably by filtration, very particularly preferably by filtration using a solid-liquid filter.

The further separation of the liquid constituents into styrene monomers and further constituents preferably comprises at least one step of distillation, such as for example fractional distillation, at least one step of chromatography, such as for example column chromatography, HPLC or flash chromatography, and/or at least one step of crystallization, such as for example fractional crystallization. Particularly preferably, the separation of the liquid constituents comprises at least one step of distillation, very particularly preferably at least one step of fractional distillation. In a very particularly preferred embodiment, the separation of the liquid constituents into styrene monomers and further components comprises at least one step of fractional distillation in one or more rectifying columns.

It is often advantageous to recycle at least a portion of the further components into the reaction zone (R) the pyrolysis reactor (P). This is advantageous in particular when a portion of the further constituents contains styrene oligomers such as for example styrene dimers and styrene trimers. This allows an overall better yield of styrene monomers since the depolymerization of the remaining oligomers is made possible as a result as well. For this reason, it is preferable for at least a portion of the further components of the condensed product mixture (K), which have been separated from styrene monomers, to be recycled into the reaction zone (R) of the pyrolysis reactor (P). Particular preference is given here to a continuous recycling of the further components.

In a preferred embodiment, the further components which are recycled into the reaction zone (R) of the pyrolysis reactor (P) essentially consist of styrene oligomers, preferably of styrene dimers and styrene trimers. In this context, "essentially" means that the further components which are recycled into the reaction zone (R) of the pyrolysis reactor (P) do not contain any further components which disrupt the depolymerization process in the reaction zone (R) of the pyrolysis reactor (P) besides styrene oligomers.

The invention further provides the use of a fluidized bed reactor for the depolymerization of polystyrene at a temperature in the reaction zone (R) of from 400° C. to 1000° C. and with an average residence time of the polystyrene in the reaction zone (R) of from 0.01 s to 10 s.

The fluidized bed reactor in the reaction zone (R) preferably comprises a fluidized bed of silicon carbide (SiC). Particularly preferably, the silicon carbide, the temperature in the reaction zone (R) and the average residence time of the polystyrene in the reaction zone (R) are selected such as has been described for the process according to the invention.

The invention moreover also provides an apparatus for conducting the process according to the invention for the production of styrene monomers, in which the reaction zone (R) and the pyrolysis reactor (P) are configured such that gentle depolymerization of polystyrene is possible.

The apparatus preferably comprises, as pyrolysis reactor (P), a fluidized bed reactor, particularly preferably a fluidized bed reactor comprising a fluidized bed of silicon carbide (SiC) in the reaction zone (R), where the silicon carbide preferably has a weight-average particle size of from 20 to 1000 µm, particularly preferably 40 to 500 µm, optionally resistive heating conductors on the external walls of the reaction zone (R), an evaporator for producing steam, a steam superheater for setting the desired steam temperature, a pipe for introducing the steam into the reaction zone (R) and also a quencher for cooling down the product mixture (G).

The invention will now be illustrated by the following examples, figures and claims.

EXAMPLES

The polymer is metered from an inertized reservoir vessel (B101) via volumetric metering into a gas jet, which conveys the particles pneumatically into the reaction zone of a fluidized bed reactor (R101) containing SiC particles. The heat energy is input into the reaction zone via resistive heating conductors through the metallic reactor wall. The steam for producing the fluidized bed is provided by an evaporator (D101) and is brought to the desired temperature via a steam superheater (E102).

In the reaction zone, the SiC fluidized bed is produced with the steam and the polymer particles conveyed in pneumatically are mixed in the fluidized bed and ultimately depolymerized.

The product mixture of the depolymerization process from (R101) is cooled to below 50° C. in the column (K101) in a water mist. In the process, the condensable constituents are condensed according to their vapor pressures and are collected with the water in the cooled bottom. Solid particles are also deposited with the mist according to their coalescence tendency.

Floating, water-insoluble constituents are transferred into a buffer vessel via a skimmer system. Samples are filled of the concentrated, organic fraction of the condensed product mixture. These are measured by gas chromatography.

The water from the condensation process is cooled via a heat exchanger and then sent back into the cooling column (K101) using the pump. Solids are optionally removed via a solid-liquid filter.

Examples 1.1 to 1.6

An amorphous polystyrene (GPPS) (INEOS Styrolution, Frankfurt) with a melt volume-flow rate (Melt Volume Rate 200°/5 kg load, ISO 1133) of around 28 cm³/10 min was depolymerized in the apparatus described above under various conditions. Here, the temperature in the reaction zone of the fluidized bed reactor (R101) was varied in the range from 550° C. to 650° C. and the residence time was varied in the range from 0.46 to 1 s. Unless stated otherwise, the concentration of the polymer composition in the reaction zone was maintained at 5% by weight, based on the total charge of the reactor, consisting of SiC particles and polymer particles. The yields of pyrolysis oil (condensate oil) and of styrene monomers depending on the reaction conditions are presented in table 1. The compositions of the pyrolysis oil are presented in table 2.

Example 2

Example 1.2 was repeated with a high impact amorphous polystyrene (HIPS) (INEOS Styrolution, Frankfurt) with a melt volume-flow rate (Melt Volume Rate 200° C./5 kg load, ISO 1133) of around 4 cm³/10 min. The yield of styrene monomers is presented in table 1. The composition of the pyrolysis oil is presented in table 2.

Example 3

Example 1.1 was repeated with a polymer composition consisting of 50% by weight of the polymer composition from Example 1 and 50% by weight of the polymer composition from Example 2. The yield of styrene monomers is presented in table 1. The composition of the pyrolysis oil is presented in table 2.

TABLE 1

Results of the pyrolysis experiments

| Example | Polymer | Temperature in the reaction zone [° C.] | Average residence time in reaction zone [s] | Proportion by mass of the condensate oil based on mass used [% by weight] | Styrene concentration in the condensate oil [% by weight] |
|---|---|---|---|---|---|
| 1.1 | GPPS | 550 | 0.54 | 70.6 | 74.8 |
| 1.2 | GPPS | 600 | 0.51 | 65.9 | 83.2 |
| 1.3 | GPPS | 550 | 0.46 | 64.8 | 68.2 |
| 1.4 | GPPS | 650 | 0.48 | 69.0 | 76.8 |
| 1.5 | GPPS | 550 | 0.66 | 72.3 | 76.3 |
| 1.6 | GPPS, 8% by weight in reaction zone | 550 | 0.54 | 72.5 | 73.4 |
| 2 | HIPS | 600 | 0.51 | 45.7 | 70.9 |
| 3 | 50% by weight GPPS/ 50% by weight HIPS | 550 | 0.54 | 91.9 | 70.1 |

TABLE 2

Composition of the pyrolysis oil

| Example | Styrene concentration in condensate oil [% by weight] | Dimer concentration in condensate oil [% by weight] | Trimer concentration in condensate oil [% by weight] | Concentration of other compounds in condensate oil [% by weight] |
|---|---|---|---|---|
| 1.1 | 74.8 | 8.4 | 8.3 | 8.6 |
| 1.2 | 83.2 | 6.0 | 0.6 | 10.3 |
| 1.3 | 68.2 | 10.7 | 9.8 | 11.2 |
| 1.4 | 76.8 | 4.5 | 0.7 | 17.9 |
| 1.5 | 76.3 | 7.0 | 5.3 | 11.3 |
| 1.6 | 73.4 | 8.2 | 1.1 | 17.3 |
| 2 | 70.9 | 7.3 | 3.3 | 18.6 |
| 3 | 70.1 | 6.6 | 7.5 | 15.7 |

Figure 1:
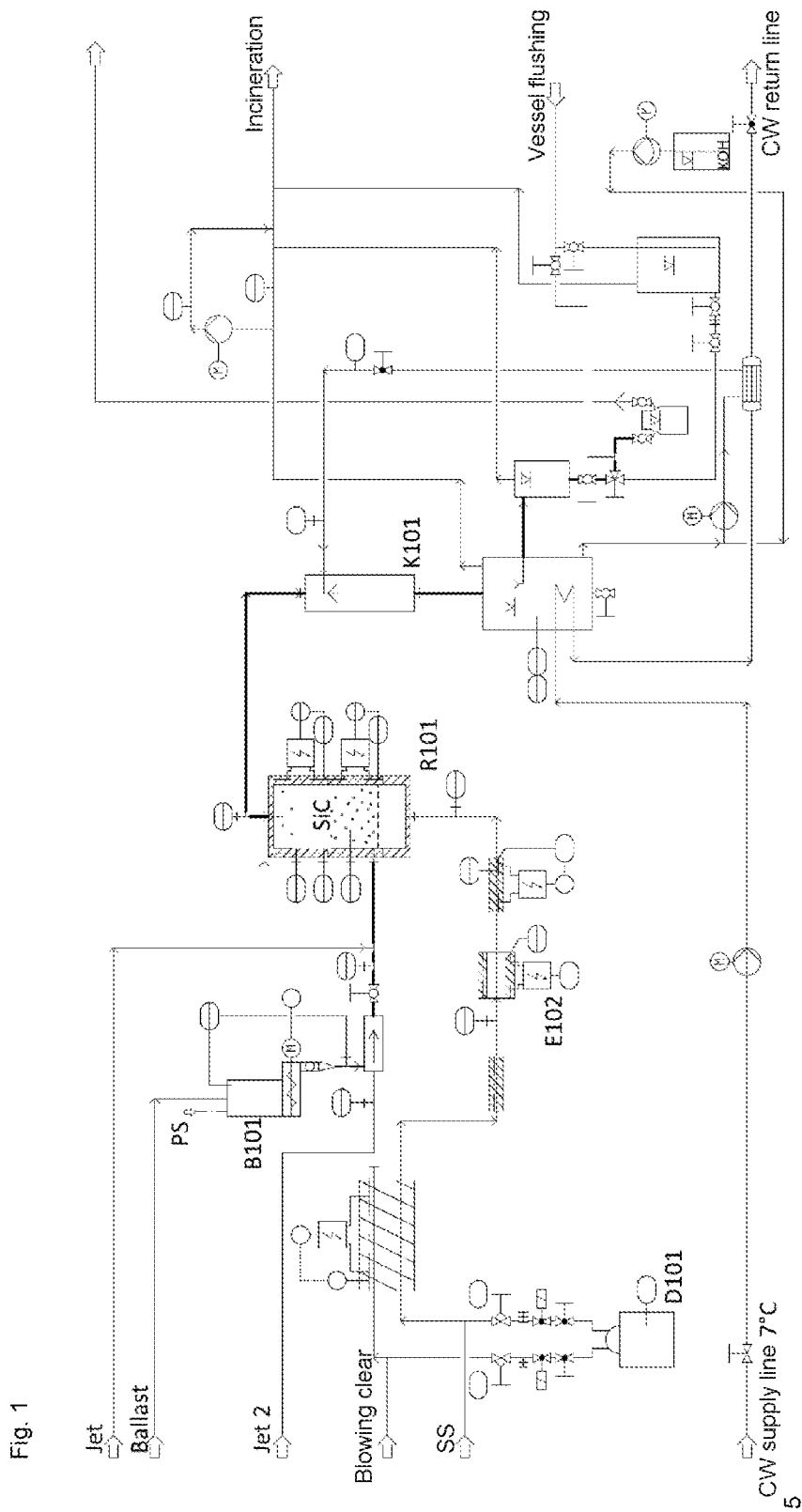
FIG. 1 shows a flow diagram of the pilot plant for carrying out the production of styrene monomers by depolymerization of polystyrene
Figure 2:
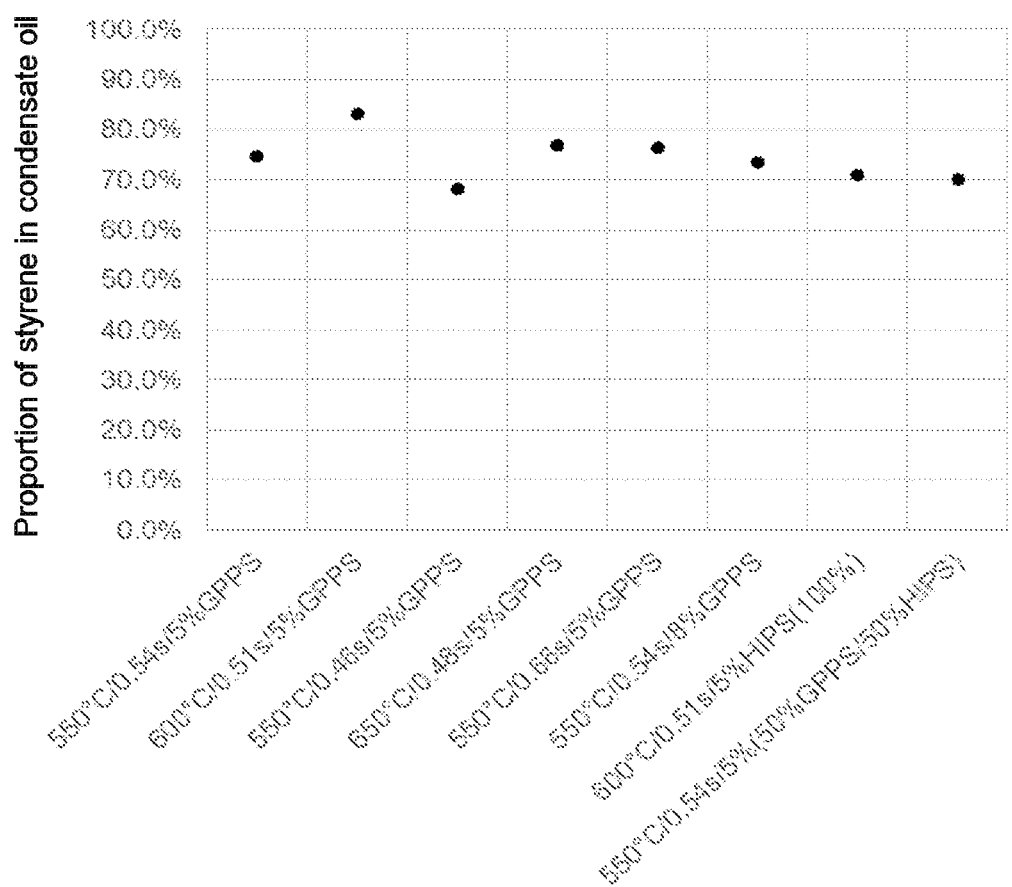
FIG. 2 shows an overview of the styrene concentration in the condensate oil.
Figure 3:
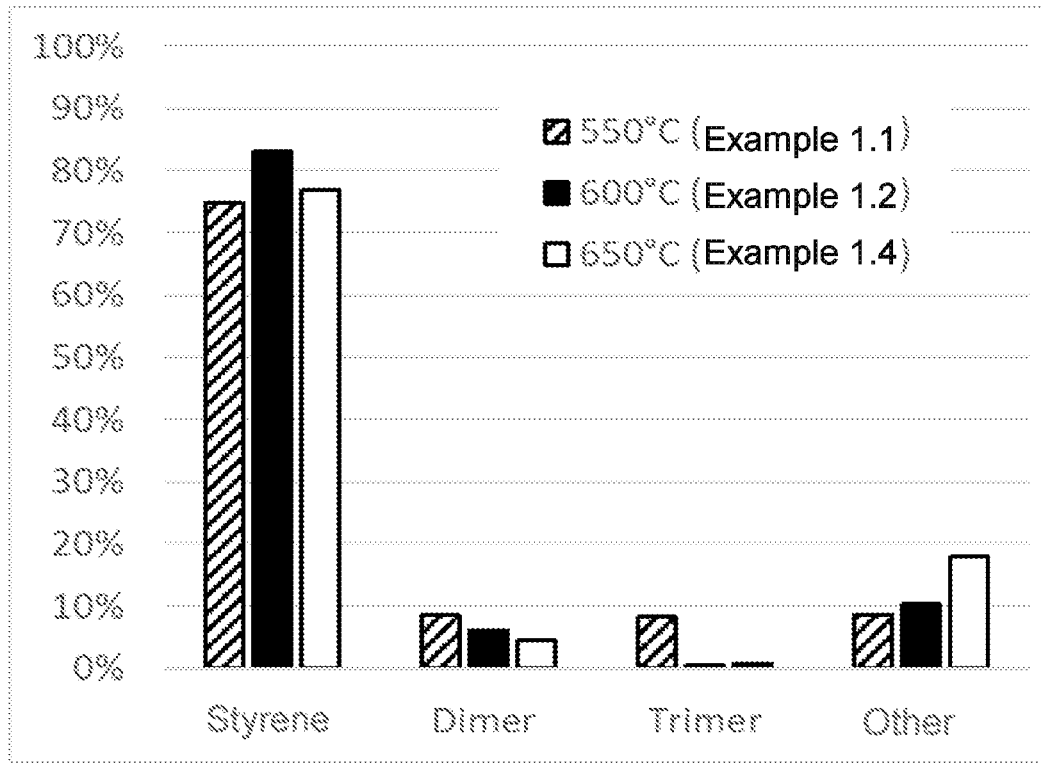
FIG. 3 shows the dependence of the pyrolysis oil composition on the temperature.
Figure 4:
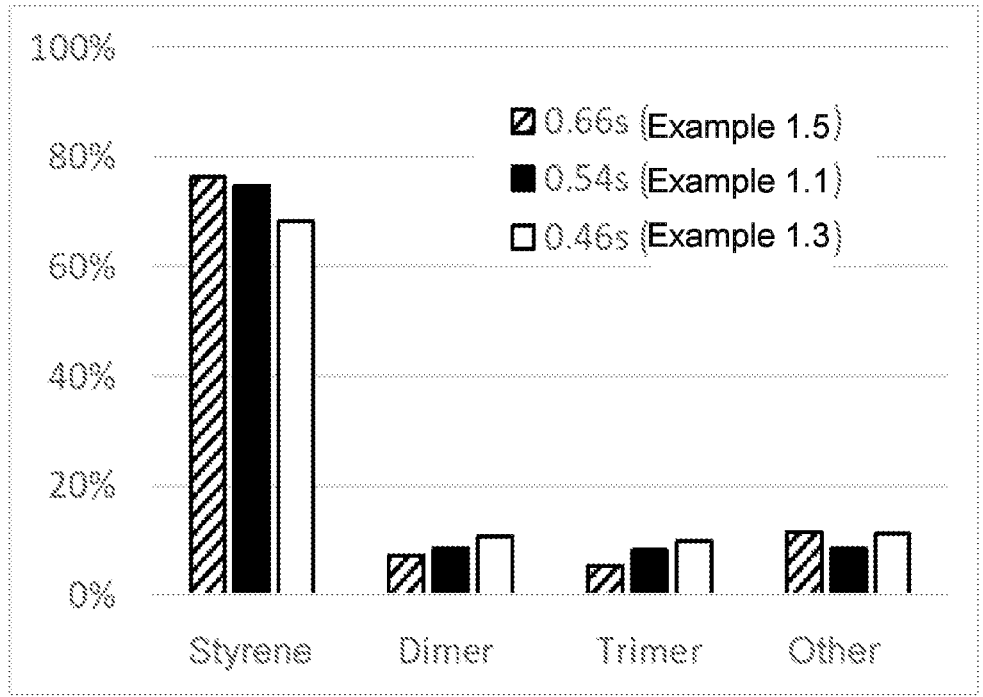
FIG. 4 shows the dependence of the pyrolysis oil composition on the residence time in the case of pure GPPS.
Figure 5:
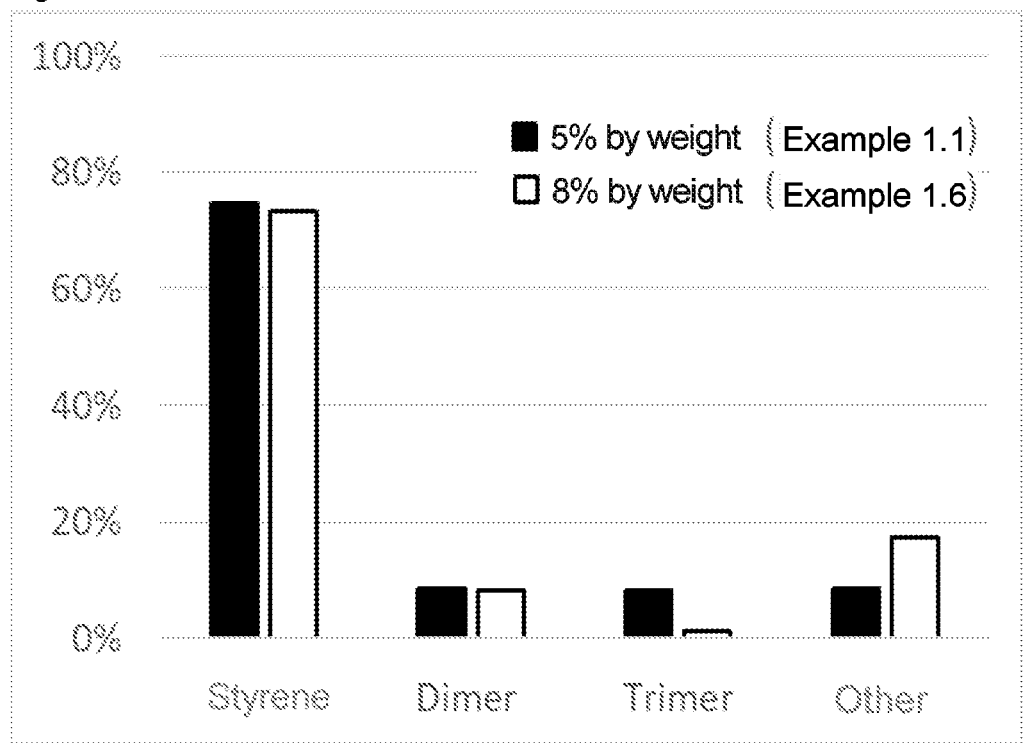
FIG. 5 shows the dependence of the pyrolysis oil composition on the concentration of the reaction material in the reactor.
Figure 6:
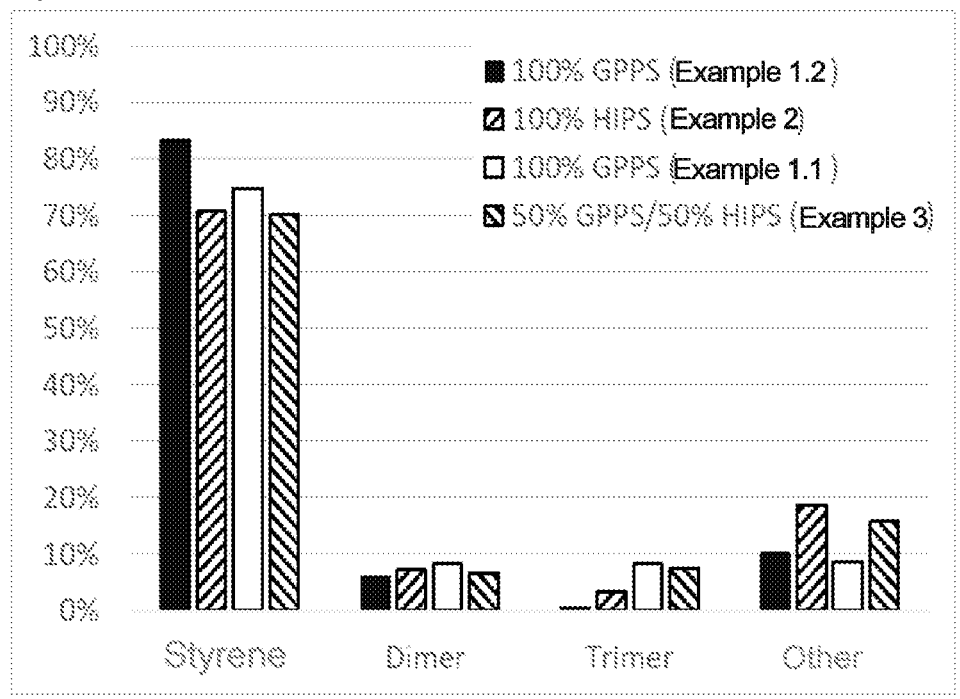
FIG. 6 shows the dependence of the pyrolysis oil composition on the composition of the reaction material.

The invention claimed is:
1. A process for the production of styrene monomers by depolymerization of polystyrene, comprising the steps of:
    a) feeding a polymer composition (A) containing 60% to 99.9% by weight of a polystyrene, based on the total weight of the polymer composition (A), into the reaction zone (R) of a pyrolysis reactor (P);

b) thermally cleaving the polystyrene present in the polymer composition (A) in the reaction zone (R) of the pyrolysis reactor (P) at a temperature of from 400° C. to 1000° C., to obtain a product mixture (G) containing styrene monomers and further components;

c) withdrawing the product mixture (G) obtained in step b) from the reaction zone (R) of the pyrolysis reactor (P);

d) cooling the product mixture (G) withdrawn in step c), to obtain a condensed product mixture (K) containing styrene monomers and further components; and e) separating the styrene monomers from the further components of the condensed product mixture (K) obtained in step d), wherein the average residence time (Z) of the polymer composition (A) in the reaction zone (R) of the pyrolysis reactor (P) is from 0.01 s to 10 s, wherein the pyrolysis reactor (P) is a fluidized bed reactor, and wherein the reaction zone (R) of the fluidized bed reactor comprises a fluidized bed comprising silicon carbide.

2. The process of claim 1, wherein the temperature in the reaction zone (R) of the pyrolysis reactor (P) is 580° ° C. to 630° C. and the average residence time (Z) of the polymer composition (A) in the reaction zone (R) of the pyrolysis reactor (P) is 0.4 s to 0.6 s.

3. The process of claim 1, wherein the condensed product mixture (K) obtained in step d) contains from 75% to 99% by weight of styrene and 1% to 25% by weight of the further components, based on the total weight of the condensed product mixture (K).

4. The process of claim 1, wherein at least a portion of the further components obtained in step e) is recycled into the reaction zone (R) of the pyrolysis reactor (P).

5. The process of claim 4, wherein the further components obtained in step e) which are recycled into the reaction zone (R) of the pyrolysis reactor (P) consist essentially of styrene oligomers.

6. The process of claim 4, wherein the recycling of the further components obtained in step e) into the reaction zone (R) of the pyrolysis reactor (P) is continuous.

7. The process of claim 1, wherein the polystyrene component in the polymer composition (A), which in step a) is fed into the reaction zone (R) of the pyrolysis reactor (R), consists essentially of general purpose polystyrene (GPPS).

8. The process of claim 1, wherein in step d), the product mixture (G) withdrawn in step c) is cooled to a temperature of from 0° ° C. to 50° C.

9. The process of claim 1, wherein the polymer composition (A) containing polystyrene in step a) does not contain any further polymeric components.

10. The process of claim 1, wherein the separation of the styrene monomers in step e) comprises a step of fractional distillation.

11. An apparatus for conducting the process of claim 1, wherein the reaction zone (R) and the pyrolysis reactor (P) are configured such that gentle depolymerization of polystyrene is possible, wherein the pyrolysis reactor (P) is a fluidized bed reactor, and wherein the reaction zone (R) of the fluidized bed reactor comprises a fluidized bed comprising silicon carbide.

12. The process of claim 1, wherein in step d) the cooling of the product mixture (G) is carried out by contacting the product mixture (G) with a water mist.

13. The process of claim 12, wherein the condensed product mixture (K) obtained in step d) is obtained in a two-phase system, wherein the water mist is the aqueous phase of the two-phase system and the condensed product mixture (K) is separated from the aqueous phase as the floating organic phase of the two-phase system.

14. The process of claim 13, wherein the aqueous phase is cooled again and recycled as the water mist.

15. The process of claim 14, wherein a base is added to the aqueous phase that is cooled again and recycled as the water mist.

16. The process of claim 15, wherein the base is KOH.

17. A process for the depolymerization of a polystyrene comprising the use of a fluidized bed reactor with a temperature in a reaction zone (R) of from 400° C. to 1000° C. and with an average residence time (Z) of the polystyrene in the reaction zone (R) of the fluidized bed reactor of from 0.01 s to 10 s, wherein the fluidized bed reactor comprises a fluidized bed comprising silicon carbide, the process comprising a step of feeding the polystyrene to the reaction zone (R) of the fluidized bed reactor.

18. The process of claim 17, wherein the temperature in the reaction zone (R) of the fluidized bed reactor is 580° C. to 630° C. and the average residence time of the polymer composition (A) in the reaction zone (R) of the fluidized bed reactor is 0.4 s to 0.6 s.

* * * * *